United States Patent
Peterson

(10) Patent No.: US 10,881,298 B2
(45) Date of Patent: Jan. 5, 2021

(54) METHOD AND APPARATUS FOR METAL IMPLANT CONTACT DETECTION THROUGH CAPACITIVE MEASUREMENTS

(71) Applicant: Garwood Medical Devices, LLC, Buffalo, NY (US)

(72) Inventor: Brian R. Peterson, Buffalo, NY (US)

(73) Assignee: Garwood Medical Devices, LLC, Buffalo, NY (US)

( * ) Notice: Subject to any disclaimer, the term of this patent is extended or adjusted under 35 U.S.C. 154(b) by 0 days.

(21) Appl. No.: 16/862,665

(22) Filed: Apr. 30, 2020

(65) Prior Publication Data

US 2020/0253478 A1 Aug. 13, 2020

Related U.S. Application Data

(62) Division of application No. 16/107,681, filed on Aug. 21, 2018, now Pat. No. 10,638,931.

(Continued)

(51) Int. Cl.
*A61L 27/04* (2006.01)
*A61B 5/06* (2006.01)
(Continued)

(52) U.S. Cl.
CPC ............ *A61B 5/0031* (2013.01); *A61B 5/061* (2013.01); *A61B 5/686* (2013.01); *A61L 27/04* (2013.01);
(Continued)

(58) Field of Classification Search
CPC . A61B 5/061; A61B 5/06–064; A61B 5/0031; A61B 5/686; A61L 27/04–06; A61F 2002/488
See application file for complete search history.

(56) References Cited

U.S. PATENT DOCUMENTS

| | | | |
|---|---|---|---|
| 5,009,644 A | 4/1991 | McDonald | |
| 2009/0216182 A1 | 8/2009 | Lauchard | A61M 5/20 604/65 |
| 2009/0322557 A1 | 12/2009 | Robb et al. | |
| 2010/0217244 A1 | 8/2010 | Mann et al. | |
| 2010/0332158 A1 | 12/2010 | Courtial | G06F 11/284 702/55 |
| 2012/0116149 A1 | 5/2012 | Pilla et al. | |

(Continued)

FOREIGN PATENT DOCUMENTS

| | | |
|---|---|---|
| CN | 107850649 A | 3/2018 |
| WO | WO 2016/206969 A1 | 12/2016 |

OTHER PUBLICATIONS

International Search Report and Written Opinion for PCT/US18/47527; dated Nov. 7, 2018; 5 pages.

(Continued)

*Primary Examiner* — Thaddeus B Cox
(74) *Attorney, Agent, or Firm* — Barclay Damon LLP

(57) ABSTRACT

A method and apparatus for metal implant contact detection through capacitive measurements is provided. Capacitive measurement is accomplished with a conductive wire/lead, for example a main needle. The measured capacitance increases as the main needle is moved through the skin and tissues, then jumps when the main needle makes contact with the metal implant, thus proving the metal implant exists as well as detecting the location of the metal implant. The jump in capacitive measurement is detectable because the area of capacitance has increased from the main needle alone to the main needle plus the surface area of the metal implant. The apparatus can include a reference needle for taking reference needle capacitive measurements in the tissues surrounding the metal implant to increase the accuracy during use of the apparatus. A housing is provided for supporting the main and reference needles and supporting or housing apparatus electronics.

12 Claims, 4 Drawing Sheets

Related U.S. Application Data

(60) Provisional application No. 62/548,831, filed on Aug. 22, 2017.

(51) Int. Cl.
*A61F 2/48* (2006.01)
*A61B 5/00* (2006.01)
*A61N 1/378* (2006.01)

(52) U.S. Cl.
CPC ............... *A61B 2560/0214* (2013.01); *A61B 2562/0214* (2013.01); *A61F 2002/482* (2013.01); *A61F 2002/488* (2013.01); *A61N 1/3787* (2013.01)

(56) References Cited

U.S. PATENT DOCUMENTS

| | | | |
|---|---|---|---|
| 2012/0289819 A1 | 11/2012 | Snow | A61F 5/0056 600/424 |
| 2013/0167613 A1 | 7/2013 | Kokawa | G01F 25/0061 73/1.73 |
| 2014/0218028 A1 | 8/2014 | Snyder et al. | |
| 2017/0165496 A1 | 6/2017 | Pilla et al. | |
| 2018/0317818 A1 | 11/2018 | Puppels | A61B 5/1455 |

OTHER PUBLICATIONS

Chinese Office Action and Search Report for CN 201880054561.6; dated Sep. 23, 2020; 6 pages.
Canadian Office Action and Examination Search Report for CA 3,073,506; dated Oct. 21, 2020; 5 pages.

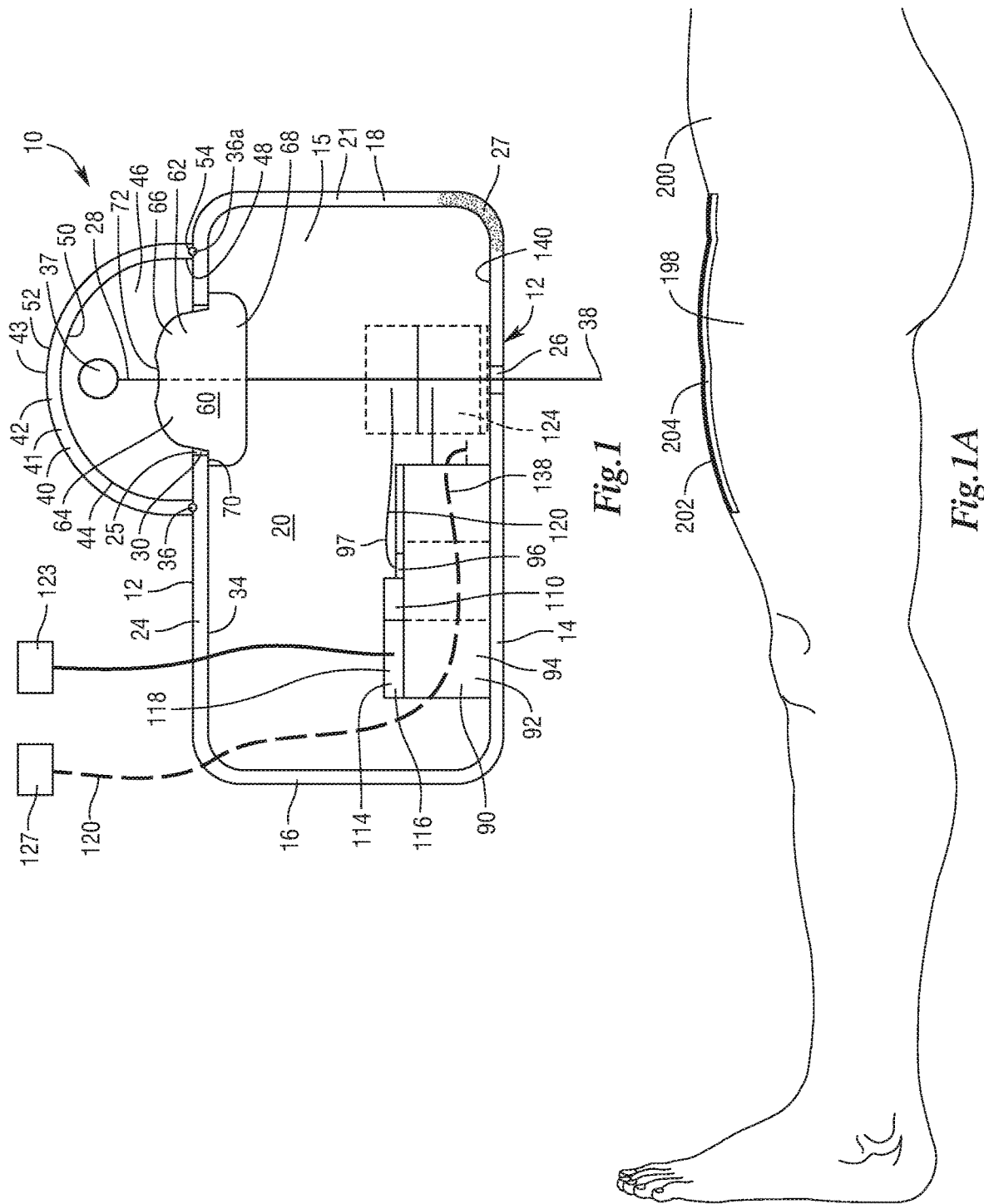

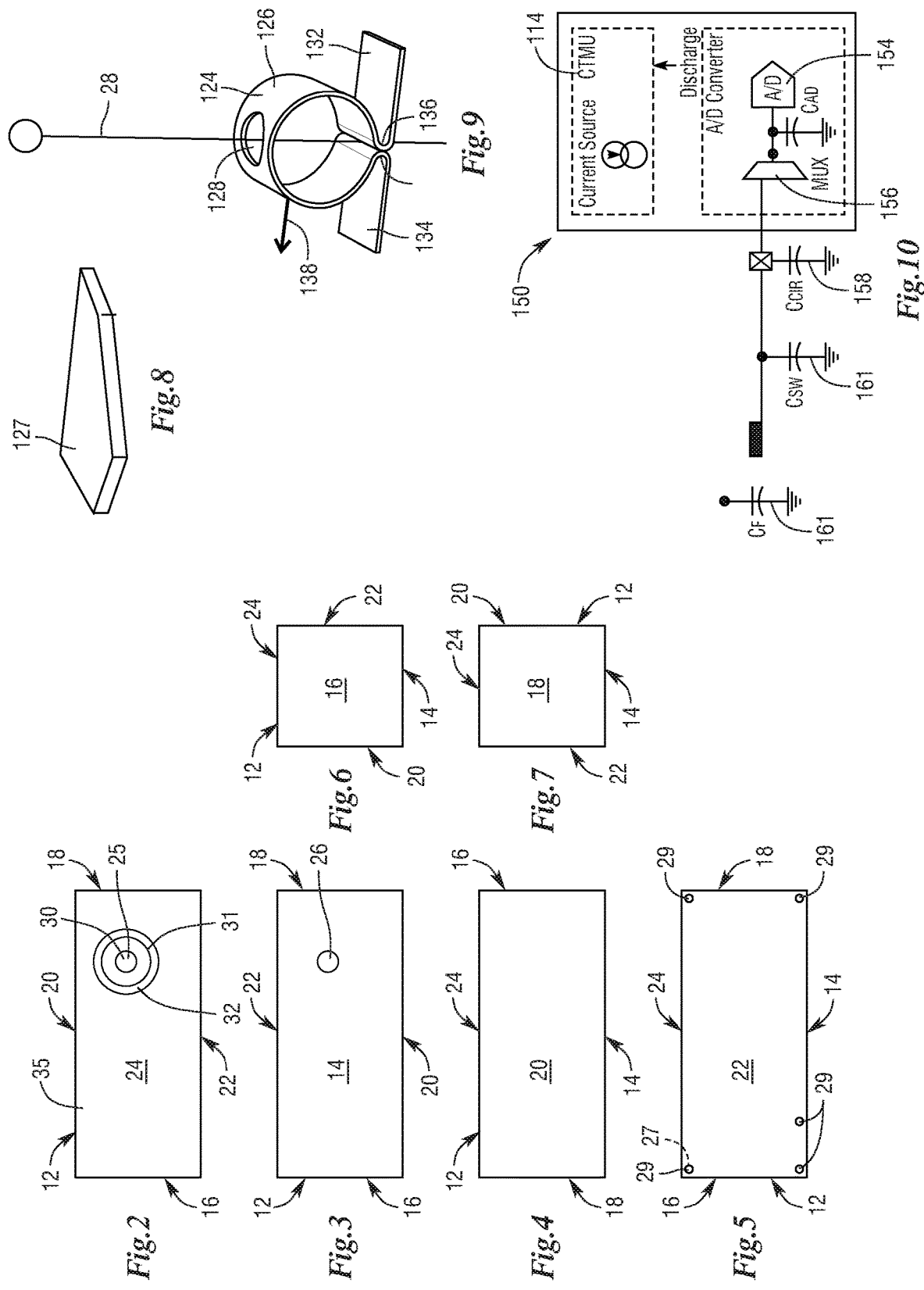

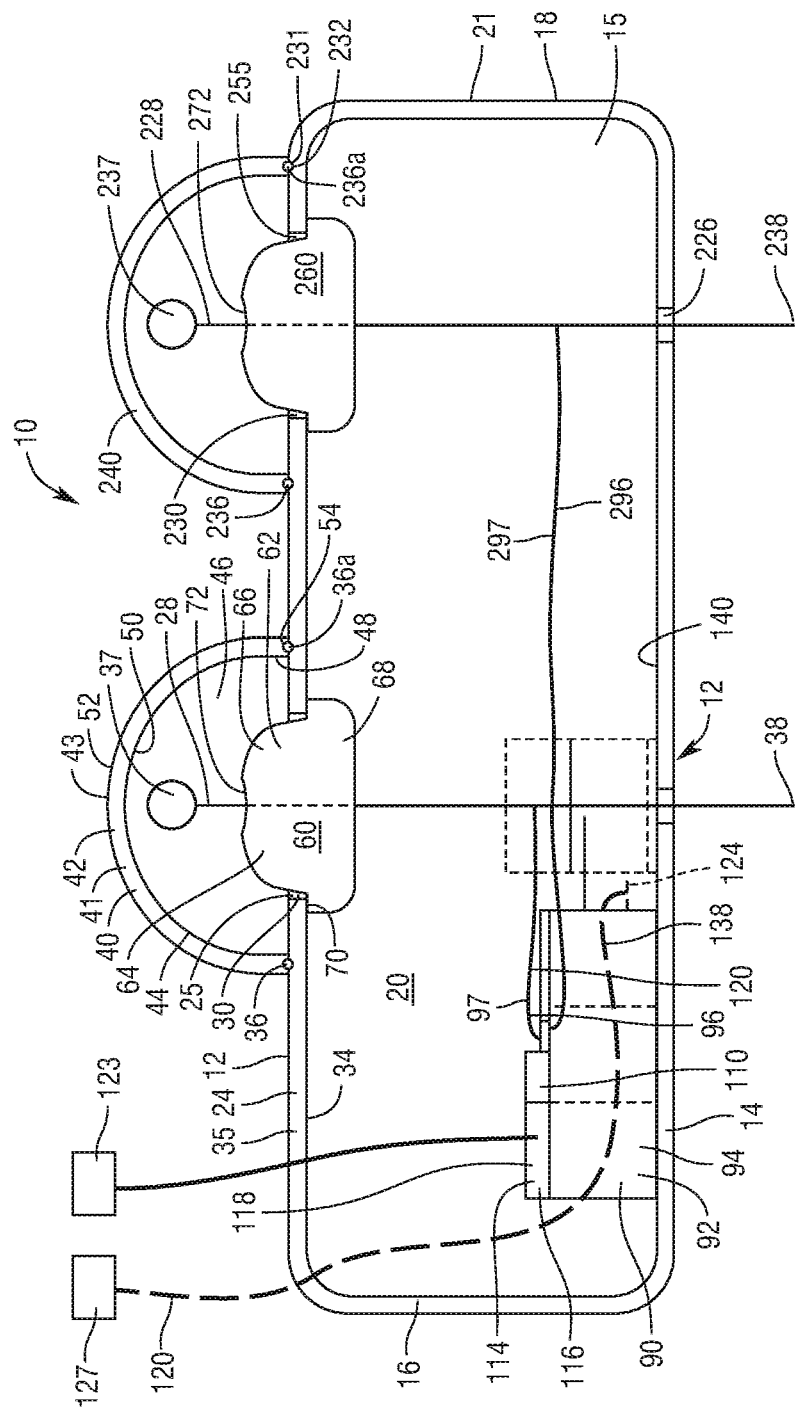

METHOD AND APPARATUS FOR METAL IMPLANT CONTACT DETECTION THROUGH CAPACITIVE MEASUREMENTS

CROSS REFERENCE TO RELATED APPLICATION

This application is a divisional application of U.S. application Ser. No. 16/107,681, filed Aug. 21, 2018, now U.S. Pat. No. 10,638,931, which claims priority under relevant portions of 35 U.S.C. § 119 to U.S. Application No. 62/548,831, filed Aug. 22, 2017. The entire contents of each application are herein incorporated by reference.

BACKGROUND

New technologies are and have been developed that involve electrical interfacing with a metal implant temporarily. One such technology involved calls for providing an electrical current through the implant in order to eliminate biofilms from the surface of the metal that would otherwise prove difficult to break up. The challenge is that the implant will already have been placed into a patient, for example implanted in the leg or knee, and the body will have already healed. In such a scenario there is no readily available access to the implant.

This means that in order to contact the implant, leads or wires would have to be inserted through the skin and one or more lead/wire will need to come into electrical contact with the metal implant. One challenge with this technique is that the implant cannot have anything attached to it, because anything attached to the implant may or will alter the functionality of the implant. Another challenge of the temporary contact is that the main needle will have to be placed in physical contact with the implant, and while this can possibly be done by feel or X-ray guidance to ensure lead/wire is touching the metal implant, there is no sufficient existing scheme or method capable of providing direct feedback that the wire/lead is actually contacting the metal implant.

Thus, what is needed is a method and apparatus that allow for the elimination of biofilms from the surface of the metal implant and that overcomes the challenges mentioned above. The apparatus should be that is easy to use, and provide for a way to detect a metal implant so, for example, biofilms can be dealt with in a suitable manner.

SUMMARY

A capacitance measuring apparatus and method for metal implant contact detection through capacitive measurements is provided. A capacitive measurement is used to detect when a conductive lead, wire, or main needle made of metal make contact with a metal implant. It is pointed out that the terms wire, lead and main needle may used interchangeably throughout this description.

When the main needle moves through the human body, for example a patient, and it makes contact with the implant there is a sudden jump or increase in the measured capacitance, and this sudden jump in measured capacitance proves that contact with the metal implant exists or is present. As the main needle moves to the implant, the capacitance increases because of the human body's capacitance, and when the main needle or lead comes into contact with the metal implant the measured capacitance will jump by a detectable amount, because the area of capacitance has gone from the main needle to the main needle plus the area of the implant. By looking specifically for this sudden jump in capacitance, it is possible to detect when the main needle has come in direct contact with the implant.

Additionally, in another embodiment a reference needle is also be provided and used in the body as a way to measure the capacitance of the human body. By comparing the capacitive measurement of the reference needle to that of the main needle, whose contact with the metal implant is needed, a more accurate detection is possible as most of the capacitance of the body will be rejected.

BRIEF DESCRIPTION OF THE DRAWING FIGURES

FIG. 1 is a front sectional view of a capacitance measuring apparatus having a main needle.

FIG. 1A is a sectional view of the skin and tissue of the body of a patient.

FIG. 2 is a top view of a housing assembly that is part of the capacitance measuring apparatus.

FIG. 3 is a bottom view of the housing assembly.

FIG. 4 is a rear view of the housing assembly.

FIG. 5 is a front view of the housing assembly.

FIG. 6 is a left side view of the housing assembly.

FIG. 7 is a right side view of the housing assembly.

FIG. 8 is a perspective view of an implant.

FIG. 9 is a perspective view of a main needle and a contact.

FIG. 10 is a schematic of a circuit that is part of and provides for control of the capacitance measuring apparatus.

FIG. 11 is a front sectional view of the capacitance measuring apparatus further including a reference needle.

DESCRIPTION

Figure 12:
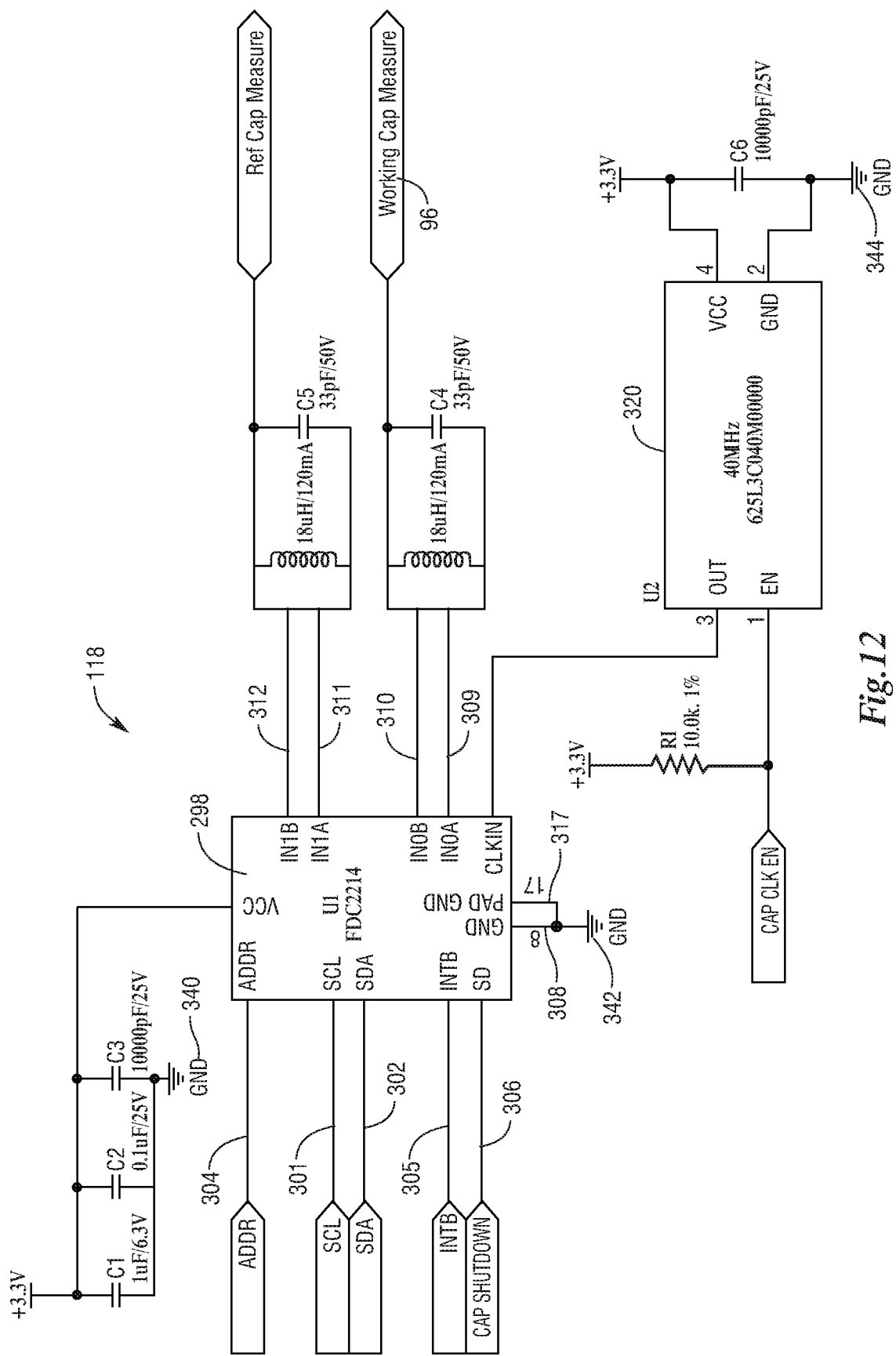
FIG. 12 is a diagrammatic view showing circuitry operatively associated with the main needle and the reference needle.

FIG. 1 shows a sectional view of a capacitance measuring an apparatus 10. The capacitance measuring an apparatus 10 includes a housing 12 as shown in FIGS. 1-7. The housing 12 includes a base wall 14 and an opposed cover wall 24 that faces the base wall 14. As shown in 1, 2-3 and 6-7, the housing 12 also includes opposed first and second end walls 16, 18. As shown in FIGS. 1, 4 and 5, the housing 12 also includes opposed first and second cross walls 20, 22. The opposed first and second end walls 16, 18 extend from the base wall 14 to the cover wall 24, and the opposed first and second cross walls 20, 22 extend from the base wall 14 to the cover wall 24. Thus, the opposed first and second cross walls 20, 22 meet with the opposed first and second end walls 16, 18, and meet with the cover wall 24, and the opposed first and second cross walls 20, 22 meet with the opposed first and second end walls 16, 18, and meet with that base wall 14.

In one embodiment the second cross wall 22 is secured, or in another embodiment or is releaseably secured, to the opposed first and second end walls 16, 18, the cover wall 24, and the base wall 14 with adhesives 27 as shown in FIG. 1. In another embodiment the second cross wall 22 is secured to the opposed first and second end walls 16, 18, the cover wall 24, and the base wall 14 with fasteners 29 as shown in FIG. 5, for example screws. In another embodiment the first cross wall 20, the opposed first and second end walls 16, 18, the cover wall 24, and the base wall are made or formed as a one piece body 21 as indicated by the dashed line in FIG. 1. The housing 12 may be embodied to have other shapes.

The housing 12 also defines a housing interior 15 that is defined by the opposed base and cover walls 14, 24, the first and second end walls 16, 18, and the first and second cross walls 20, 22. Removal of the second cross wall 22 allows access to the housing interior 15 as shown in FIG. 1.

As shown in FIGS. 1 and 3, the capacitance measuring an apparatus 10 also has a main needle 28 having a head 37 and an opposed main needle tip 38, and the base wall 14 defines a base wall opening 26 that is sized such that the main needle 28 can move through the base wall opening 26. The main needle 28 is made of metal. As shown in FIG. 3, the cover wall 24 has a cover surrounding wall 25 that defines a cover wall opening 30, and the cover wall 24 has opposed interior and exterior cover wall surfaces 34, 35, and the exterior cover wall surface 35 has an annular shaped recessed wall 31 that defines an annular gasket recess 32. The cover opening 30 is centrally located relative to the annular shaped recessed wall 31. That is, the annular shaped recessed wall 31 surrounds or encircles the cover wall opening 30 as shown. As shown in FIG. 1, the capacitance measuring an apparatus 10 includes a gasket 36 that is capable of being fitted in the annular gasket recess 32, and in one embodiment the gasket 36 is an O-ring gasket 36a. In other embodiments the annular shaped recessed wall 31 can be differently shaped and the annular gasket recess 32 can be differently shaped, so long as the gasket is capable of being fitted in the gasket recess, and all of these embodiments are intended to be within the scope and spirit of the appended claims. In addition and as shown in FIG. 1 the cover wall opening 30 and the base wall opening 26 are aligned with respect to one another, for example, in the view shown in FIG. 1 the cover wall opening 30 is vertically aligned with the base wall opening 26.

The capacitance measuring an apparatus 10 also includes a protective cover 40 that is made from plastic 41 and in one embodiment the plastic 41 is hard, and may be clear, or tinted or otherwise colored. In one embodiment the protective cover 40 has a half sphere shape 44 and defines a protective cover interior 46. The protective cover 40 also has a cover end wall 48 that may be planar, and opposed interior and exterior protective cover surfaces 50, 52. The protective cover 40 has a recessed cover portion 53 that extends from the cover end wall 48, and the recessed cover portion 53 has a gasket engagement surface 54. The gasket 36 is fitted between the recessed cover portion 53 and the annular shaped recessed wall 31, such that the protective cover 40 is secured to the cover wall 24 of the housing 12, that is, the protective cover 40 and the cover wall 24 are interlocked to one another by the gasket 36. In another embodiment adhesives 27 may be used to secure the protective cover 40 to the cover wall 24, and in such an embodiment the recessed cover portion 53 and the annular shaped recessed wall 31 would be absent. The main needle 28 has a main needle tip 38, and may have a main needle head 37, and a portion of the main needle 28 and the main needle head 37 are located in the cover interior 46.

The capacitance measuring an apparatus 10 also includes a stabilizer component 60 that is for stabilizing the main needle 28, and the stabilizer component 60 is made from silicone 62 in one embodiment. The stabilizer component 60 may be made from other materials, for example elastomeric materials, plastics and metal in other embodiments. The stabilizer component 60 has a convex stabilizer portion 64 having a convex surface 66, and has a base stabilizer portion 68 that extends from the convex stabilizer portion 64. The base stabilizer portion 68 also has an abutting surface 70. The stabilizer component 60 defines a stabilizer opening 72 that is sized such that the main needle 28 can be moved through the stabilizer opening 72. In one embodiment the stabilizer component 60 abuts against the main needle 28 to prevent the main needle 28 from moving off course as the main needle 28 is moved into the body 198 of a patient 200, with FIG. 1A showing the body 198 of the patient 200.

As shown in FIG. 1, the stabilizer component 60 is fitted in the cover wall opening 30 such that the convex stabilizer portion 62 abuts the surrounding cover wall 25 (FIG. 2) formed in the cover wall 24. At the same time, the abutting surface 70 of the base stabilizer portion 68 abuts the interior cover wall surface 34 of the cover wall 24 as shown in FIG. 1. The stabilizer component 60 is secured to the surrounding cover wall 25 with a friction fit or a pressure fit between the surrounding cover wall 25 and the convex surface 64 of the convex stabilizer portion 62. In other embodiments adhesives 27 may also be used to secure the abutting surface 70 to the interior cover wall surface 34 such that the stabilizer component 60 is secured to the cover 24, or is secured by utilizing combinations of the above.

As shown in FIG. 1, the capacitance measuring an apparatus 10 also includes a battery 92 that is positioned in the housing interior 15 of the housing 12, and the battery 92 may be embodied as a coin cell battery 94 (indicated by the dashed line in FIG. 1). The battery 92 is supported on the base wall 14. Batteries and coin cell batteries are well known to those having ordinary skill in the art and are therefore not described in greater detail herein.

The capacitance measuring an apparatus 10 takes capacitive measurements, generally indicated by reference numeral 96, and the capacitive measurements 96 can be obtained by way of a capacitance wire 97 that connects or is wired to the main needle 28. The capacitive measurements 96 are processed by the to the apparatus electronics 118. The capacitance measurements 96 are taken over time to detect when the main needle 28 is touching or contacts a metal implant 100 (the metal implant 100 shown in FIG. 8). The housing 12 can be pushed to move the main needle 28 through the skin 202 and tissues 204 with the main needle 28 being held in place by the stabilizer component 60. The above-described construction allows for the main needle 28 to be used for taking capacitive measurements 96 as the main needle 28 moves through the skin 202 of the patient 200, through the tissues 204 of the patient 200, and through the body 198 of the patient 108, and when the main needle 28 contacts the metal implant 100. This significantly reduces the cost of the main needle 28, because any traditional metal main needle 28 can be used. In addition, the same main needle 28 is used for the emitting an electrical signal to the metal implant 100 is used for the detection of the metal implant 100. In this embodiment one puncture wound is made in the patient 200, but also drastically simplifies the procedure as it eliminates the need for an introducer (not shown).

For background purpose, it is noted that humans have a measureable capacitance, for example, this commonly known phenomena is used in connection with touch screen electronic devices. Here, capacitance measurements 96 change when the main needle makes contact with a human because humans have a measureable capacitance. When the main needle 28 comes into contact with skin 202 the capacitance measurements 96 will shift, and then as the main needle 28 penetrates the skin 202 and muscles and tissues 204 of the patient 200 the capacitance measurements will 96 continue to shift. When the main needle 28 first comes into contact with the skin 202, the capacitance immediately increases or jumps in, for example, one microsecond. As the main needle 28 moves through the body 198 it either stays the same or shifts to increased capacitance depending on how deep the main needle 12 is moved.

At times it may be difficult to detect whether or not the main needle 28 is contacting skin 202 and body tissue 204, or contacting the metal implant 100. Thus, the capacitance measuring an apparatus 10 also includes capacitance measuring software 110 that is employed to detect the metal implant 100. While the capacitance measuring software 110 can take or detect capacitance measurements 96, it is also capable of rejecting or ignoring capacitance measurements 96 that do not indicated a jump or increase in capacitance. This is because the jump or increase in the capacitance measurement 96 will be less when compared to the jump or increase in the capacitance measurement 96 when the main needle 28 contacts the metal implant 100. Thus, by rejecting and ignoring the gradual climb in the capacitance measurements 96 as the main needle 28 is inserted deeper into the patient 200, the capacitance measuring software 110 allows for the a more exact location of the metal implant 100 and thus the past problems with locating metal implants 100 are avoided, and extensive medical procedures to locate metal implants 100 are no longer needed.

As shown in FIG. 1, the capacitance measuring an apparatus 10 includes a charge time measuring unit 114 (also referred to herein as a CTMU module 114) that is built into peripheral interface controller 116 (also referred to herein as a PIC microcontroller 116) that form the apparatus electronics 118 (see FIG. 4). The capacitance measuring software 110 is operatively associated with the PIC microcontroller 116. The battery 92 powers these components. The battery 92, the CTMU module 114 and the PIC microcontroller 116 are all located in the housing 12. As shown in FIG. 1 the peripheral interface controller 116 is wired to a suitable output device 123, for example a screen display. Those having ordinary skill in the art know the details pertaining to how this type of capacitance measuring is accomplished. CTMU modules 114 and PIC microcontrollers 116, and their use and operation known to those having ordinary skill in the art and they are therefore not described in greater detail herein.

As show in FIG. 10, the capacitance measuring an apparatus 10 has control circuit 150. The control circuit 150 includes a current source 152 and the CTMU module 114 and an analog to digital converter 154 (sometimes referred to herein A/D converter 154). The AD converter 154 is in communication with a multiplexer 156 (sometimes referred to herein as MUX 156) that is wired to a circuit capacitor 158 (sometimes referred to herein as CCIR 158). The circuit capacitor 158 is wired to a switch capacitor 160 (sometimes indicated by CSW 160). Spaced from the CSW 160 is a parallel capacitor 161 (sometime indicated by CF 161). In use, the control circuit 150 can detect when the main needle 28 is moved closer of farther from the metal implant 100, and detects when the main needle 28 contacts the main implant 100.

There are a plurality ways to connect the apparatus electronics 118 with the main needle 28, for example directly wiring to the main needle 12 to the apparatus electronics 118 with the capacitance wire 97 as shown in FIG. 1 is one option.

In another embodiment the capacitance measuring an apparatus 10 and can be monitored wirelessly. In such an embodiment the apparatus electronics 118 run the previously mentioned capacitance measuring software 110. The apparatus electronics 118 are capable of outputting the capacitance measurement output data 120 to any suitable electronic device 127, for example a laptop computer, a screen display, a database, and other devices, including outputting capacitance measurement output data 120 wirelessly.

In another embodiment the apparatus electronics 118 and battery are located external to the housing 12.

In another embodiment the capacitance measuring an apparatus 10 may further includes a metal contact 124 as shown in FIG. 1 in dashed line and in FIG. 9 in solid line. The main needle 28 makes electrical contact with the apparatus electronics 118 by use of a metal contact wire 138. The metal contact 124 has a cylindrical portion 126 that defines a spring opening 128, and has first and second opposed spring arms 130, 132 that extend from the cylindrical portion 126. The first spring arm 130 extends to a first bent spring portion 134 and the second spring arm 132 extends to a second spring bent portion 136. The first and second bent portions 134, 136 abut one another. When the main needle 28 is moved is past and through the spring opening 128 and through the first and second spring bent portions 134, 136 the main needle 28 and pushes them away from one another. At the same time the main needle 28 is pinched and stabilized by the first and second spring bent portions 134, 136. The use of the above-described metal contact 124 allows the main needle 12 to be controllably moved and guided into the patient 200, and a metal contact wire 138 is used for transmitting capacitive measurements 96 to the apparatus electronics 118. In addition, the opposed first and second spring arms 130, 132 are mounted on or otherwise secured to a base wall interior surface 140 with, for example, adhesives 27.

In use, the main needle 28 is positioned in the housing interior 15 and the user, for example a doctor (not shown) pushes on the housing 12 such that the main needle tip 38 penetrates the skin 202 and moves through the body tissues 204. At the same time capacitive measurements 96 are taken by the CTMU module 114 and processed by the capacitance measuring software 110. If there is no increase in capacitance measured, then the user will know that no metal implant 100 is in that particular area and can move the main needle 28 to another location and re-insert the main needle 28 into the patient 200. If, however, when the main needle 28 is inserted and the capacitive measurements 96 measured by capacitance measuring software 110 that contact with the metal implant 100 has been made, then the user now knows exactly where the metal implant 100 is and can use that information for virtually any other purpose, for example exploratory surgery, surgery, scanning, and monitoring.

One challenge that has been overcome is that capacitance will begin to increase rapidly as the distance from the main needle tip 38 to the metal implant 100 decreases. The capacitance measuring an apparatus 10 overcomes this by setting the thresholds, for example setting the farads from one picofarad to one nanofarad in one embodiment, and in other embodiments the farad thresholds can set from 1.3 pircofarads to 0.08 nanofarads, and in other embodiments the farad thresholds can be two picofarads, because the metal implant 100 will significantly raise the total surface area of the main needle 28 when they contact one another and significantly increase the overall capacitance being measured. This sudden rise in capacitive measurement 96 may occur in one microsecond, and in other embodiments in or more or less that one microsecond.

As shown in FIGS. 1 and 11, in another embodiment the capacitance measuring apparatus 10 further includes a reference needle 228, a reference needle protective cover 240, and a reference needle stabilizer component 260 that defines a reference need stabilizer component opening 272. Thus, in this embodiment there is both the main needle 28 and a reference needle 228. In this embodiment the base wall 14 also defines a reference needle base wall opening 226, and the cover wall 24 has a second cover surrounding wall 255 that defines a second cover wall opening 230, and the cover wall 24 has opposed interior and exterior cover wall surfaces 34, 35, and the exterior cover wall surface 35 has a second annular shaped recessed wall 231 that defines an annular gasket recess 232. The second cover wall opening 230 is centrally located relative to the second annular shaped recessed wall 231. That is, the second annular shaped recessed wall 231 surrounds or encircles the second cover wall opening 230 as shown. As shown in FIG. 1, the capacitance measuring an apparatus 10 includes a second gasket 236 that is capable of being fitted in the second annular gasket recess 232, and in one embodiment the second gasket 236 is an O-ring gasket 36a. In addition and as shown in FIG. 11 the cover wall second cover wall opening 230 and the second base wall opening 226 are aligned with respect to one another, for example, in the view shown in FIG. 11 the second cover wall opening 230 is vertically aligned with the second base wall opening 226. The remainder of the components in this embodiment.

The reference needle 228 includes a reference needle head 238 and reference needle tip 238. A reference capacitance wire 297 connects the reference needle 228 to the apparatus electronics 118. The capacitance measuring software 110 is capable of comparing the capacitive measurements 96 taken from the main needle 28 and reference capacitive measurements 296 obtained from the reference needle 228. The reference needle 228 is moved into the body 198 and body tissues 204 that are near to or that surround the implant 100. The comparison of the capacitive measurements 96 and the reference capacitive measurements 296 will help eliminate the capacitance measurement of the body itself. This increases the accuracy in determining if the main needle 28 is or is not contacting the metal implant 100. For example if the capacitive measurement 96 is rapidly increased suddenly and is higher relative the reference capacitive measurement 296 it will indicate that the main needle 28 is in contact with the metal implant 100. If, on the other hand, the capacitive measurement 96 is low relative the reference capacitive measurement 296 it will indicate that the main needle 28 is in contact with the metal implant 100.

Thus, the reference needle 228 improves the accuracy of the capacitance measuring apparatus 10 improve the accuracy of a positive detection of the metal implant. It is to be understood that the remainder of the surfaces and components in this embodiment though not described in detail are substantially the same as what is shown and described in connection with FIG. 1. In addition, in this embodiment another one of the above-describe metal contacts 124 may be employed, but is not shown herein for the sake of clarity, to further contact and stabilize the reference needle 228.

As shown in FIG. 12 the apparatus electronics 118 further include a first converter 298, and the first converter 298 is designated U1 that converts capacitance to a digital format. The first converter 298 may be embodied as a FDC2214 converter and converters are well known to those having ordinary skill in the art, There are also first, second and third capacitors designated C1, C2, C3 with 3.3V applied. In one embodiment the first capacitor C1 is 1 uF/6.3 V, the second capacitor C2 is 0.1 uF/25V, and the third capacitor C3 is 10000 pF/25V, and all of them extend to a first ground designated 340 and to a first voltage common collector indicated by VCC along line 307. An adder line 304 extends from the first converter 298.

Serial data (SDA) and serial clock (SCL) lines 301 and 302 extend from the first converter 298 designated U1. And, Configurable Interrupt output pipeline 305 and capacitor shutdown line 306 extend from the first converter 298.

As shown, inverter and a second ground pad along ground lines 308 and 317 extend to the first converter 298 to a second ground 342 along lines 308 and 317.

First and second IN0A and IN0B leads 309, 310 for measuring signal power and that extend from the first converter 298, and there is a first inductor designated L1 that is 18 uH/120 mA and a first capacitor designated C1 having 33 pF/50V that takes working capacitor measurements 96. C1 and L1 form an LC resonator used to measure the capacitance changes.

Third and fourth leads IN1A, 1NAB leads 311, 312 extend from the first converter 298, and there is a second inductor designated L2 that is 18 uH/120 mA and a second capacitor designated C2 having 33 pF/50V that takes reference capacitance measurements 296.

There is also an oscillator 320 that may be 340 MHz, and oscillators are well known and commercially available, for example by part number 625L3C040M00000 as shown. The oscillator 320 functions as a clock and has a 3.3V and a resistor designated R1 having a resistance of 0.1% of 10 k ohms as shown. The oscillator 320 is grounded by a third ground 344, and has a capacitor designated C6 that is 10000 pF/25V. There is a second voltage common collector designated VCC2. The oscillator 320 has a second converter designated U2 that converts capacitance to a digital form, and the second converter U2 is communication with the first converter U1 as shown.

The above configuration of the apparatus electronics 118 allow for capacitive measurements 96 to be taken by just the main needle 28 such that the metal implant 100 can be located, or can be used such that capacitive measurements 96 can be taken by both the main needle 28 and the reference needle 240.

The U1 utilizes the precision clock signal from U2 to measure the frequency difference of the LC tank and thus provide a capacitance change. Using the clock and data line and following I2C protocols, the main MCU can take the capacitance measurements. Channel 0 (INA0, INB0) is used to measure for contact with the implant and inserted after reference is placed in the body. The capacitance measurement of Channel 1 (INA1, INB1) is of the reference needle. As the working needle is placed into the body the capacitance of Channel 0 is done with Channel 1's measurement subtracted from it. The capacitance of Channel 0 will always be higher than the reference, once it is in contact with the metal implant. In addition, the change in capacitance will look for a sudden change of capacitance in the measure of 2 pF-10 nF range in less than 100 mS.

It is to be understood that all of the amounts described above, for example in farads and in capacitance, are for illustrative purposes and may be different in other embodiments and it is intended that this amounts do not limit the scope of this application.

In the past most schemes and methods for detecting capacitance required that that there be a direct electrical connection from first and second leads connected to the implant 100, followed by passing a small amount of power through the implant 100. If power flows from the first lead is detected on the lead, then that would prove that both leads are in contact with a metal implant 100. The challenge associated with this method is that two leads or a single lead with two separate electrodes is required. This increases the complexity, and cost. Another problem associated with this is that the user is unable to tell which main needle is not in direct contact with the implant, and this can result in an undesirable false negative.

Another method used involves physical feedback by feeling resistance on the main needle 12 or wire or lead. A problem with this method is that the user does not know if he or she is contacting or touching metal or bone. An X-ray may help guide the main needle, but can difficult to know for sure, because anything other than physical contact with the metal implant 100 will not work due to the need for electrical contact. Additionally x-rays are typically a 2 dimensional image and losing the depth can mean that a main needle is actually touching bone instead of metal, and MRI's are not possible due to the presence of ferrous metal on the implant.

Thus, the present capacitance measuring an apparatus 10 for metal taking capacitive measurements 96 overcomes the significant problems associated with the above-described methods and schemes.

It will be appreciated by those skilled in the art that while the capacitance measuring an apparatus 10 for metal implant contact detection through capacitive measurements is not necessarily so limited, and other examples, embodiments, uses, modifications, and departures from the embodiments, examples, uses, and modifications may be made without departing from the capacitance measuring an apparatus 10 and all such embodiments are intended to be within the scope and spirit of the appended claims.

The invention claimed is:

1. An apparatus for metal implant contact detection through capacitive measurement, the apparatus comprising:
   a housing including an interior;
   a main needle supported for movement within the interior of the housing, the main needle being made from a conductive material and having a portion extending through a wall of the housing;
   at least one battery positioned in the interior of the housing;
   apparatus electronics powered by the at least one battery and in communiciation with the main needle to apply an electrical charge to the main needle, such that a capacitive measurement can be taken as the main needle moves toward or away from a metal implant and for detecting a sudden increase in a capacitive measurement when the main needle contacts the metal implant; and
   an output device in communication with the apparatus electronics and configured for outputting each of the capacitive measurements.

2. The apparatus according to claim 1, wherein the sudden increase in a capacitive measurement occurs in less than one microsecond and for up to two picofarads of capacitance.

3. The apparatus according to claim 1, wherein an increased capacitance measurement is based on a size of the metal implant such that the larger the metal implant, the larger the sudden increase in the capacitance measurement.

4. The apparatus according to claim 1, further comprising a reference needle configured to take a reference capacitance measurement of tissues surrounding the metal implant in order to improve accuracy of a positive detection of the metal implant wherein the capacitance measurement can be compared with the reference capacitance measurement.

5. The apparatus according to claim 1, wherein the housing includes opposed first and second end walls, a base wall and an opposed cover wall, a first cross wall and an opposed second cross wall, each of the walls defining the interior of the housing.

6. The apparatus according to claim 5, wherein the cover wall defines a first cover wall opening that leads to the interior of the housing, the cover wall having an annularly shaped recessed wall that defines an annular gasket recess, and the first cover wall opening centrally located relative to the annularly shaped recessed wall, and a protective cover having a gasket engagement surface, the apparatus further comprising a gasket fitted in the annular gasket recess such that the gasket abuts against the gasket engagement surface of the protective cover and the annularly shaped recessed wall, such that the gasket is secured to the cover wall.

7. The apparatus according to claim 6, further comprising a stabilizer component that defines a stabilizer opening, wherein the protective cover defines a cover interior and the stabilizer component is fitted in the cover wall opening, the main needle extending through the stabilizer component such that the main needle is stabilized while at the same time, the main needle is capable of being slid through the stabilizer component, and wherein the base wall defines a base wall opening aligned with the cover wall opening such that the main needle is capable of extending through the base wall opening.

8. The apparatus according to claim 7, wherein the cover wall defines a second cover wall opening and a reference needle stabilizer component is fitted in the second cover wall opening, the base wall defining a base wall reference needle opening and a reference needle protective cover is mounted on the cover wall to protect a reference needle and the second cover wall is aligned with the base wall reference needle opening and the reference needle stabilizer component.

9. The apparatus according to claim 1, wherein the apparatus electronics include a charge time measuring unit and a peripheral interface controller for taking capacitive measurements as the main needle is inserted into the skin and tissues of a subject, and when the main needle contacts the metal implant.

10. The apparatus according to claim 9, further comprising capacitance measuring software, wherein the apparatus electronics further include a control circuit that provides for control of the apparatus, the control circuit including a current source, a charge time measuring unit, an analog to digital converter in communication with a multiplexer that is wired to a circuit capacitor, the circuit capacitor being wired to a switch capacitor, such that capacitance measurements can be taken as the main needle moves toward the metal implant that functions as a parallel capacitor, and the capacitance measuring software collects capacitance measurements and generates capacitance measurement output data indicative of when the main needle is moved closer or farther from the metal implant and when the main needle contacts the implant.

11. The apparatus according to claim 10, wherein the apparatus electronics are configured to take reference capacitance measurements as a reference needle is inserted into the skin and tissues of a subject, and wherein main needle and reference needle capacitance measurements are compared by the apparatus electronics to determine if the main needle is in contact with the metal implant, such that if the capacitance measurement from the main needle matches the capacitance measurement from the reference needle, then contact with the metal implant has been made.

12. The apparatus according to claim 11, further comprising metal contacts with one metal contact wired to the main needle and the apparatus electronics to take capacitance measurements, and another metal contact to take reference needle capacitance measurements.

\* \* \* \* \*